US008542844B2

(12) United States Patent
Bowden et al.

(10) Patent No.: US 8,542,844 B2
(45) Date of Patent: Sep. 24, 2013

(54) SOUND MODIFICATION SYSTEM AND METHOD

(75) Inventors: Upton Beall Bowden, Canton, MI (US); David Ming Chi, Canton, MI (US); David Alan Knechtges, Saline, MI (US); Stephen James Adams, Chelmsford (GB)

(73) Assignee: Visteon Global Technologies, Inc., Van Buren Township, MI (US)

( * ) Notice: Subject to any disclaimer, the term of this patent is extended or adjusted under 35 U.S.C. 154(b) by 29 days.

(21) Appl. No.: 13/081,859

(22) Filed: Apr. 7, 2011

(65) Prior Publication Data

US 2012/0257763 A1 Oct. 11, 2012

(51) Int. Cl.

*A61F 11/06* (2006.01)
*H03B 29/00* (2006.01)
*H04B 1/00* (2006.01)

(52) U.S. Cl.

USPC ............................... 381/71.4; 381/61; 381/86

(58) Field of Classification Search

USPC ............... 381/86, 71.4, 56, 57, 71.1, 61, 124; 701/36

See application file for complete search history.

(56) References Cited

U.S. PATENT DOCUMENTS 5,138,663 A 8/1992 Moseley
5,237,617 A 8/1993 Miller
5,371,802 A 12/1994 McDonald et al.
5,635,903 A 6/1997 Koike et al.
5,850,458 A * 12/1998 Tomisawa et al. ........... 381/71.4
6,859,539 B1 2/2005 Maeda
7,650,001 B2 1/2010 Yasushi et al.
7,773,760 B2 * 8/2010 Sakamoto et al. ........... 381/71.9
8,111,834 B2 * 2/2012 Kobayashi et al. .......... 381/71.4
2005/0038576 A1 * 2/2005 Hara et al. ...................... 701/22
2005/0100172 A1 * 5/2005 Schliep et al. ............... 381/71.4
2005/0246134 A1 * 11/2005 Nagai et al. ................... 702/182
2008/0123871 A1 5/2008 Trzmiel
2009/0028353 A1 1/2009 Kobayashi et al.
2009/0066499 A1 3/2009 Bai et al.
2009/0080672 A1 3/2009 Smith
2009/0325700 A1 12/2009 Maeda
2010/0208915 A1 * 8/2010 Lipp ............................... 381/86
2011/0044470 A1 * 2/2011 Ogata ............................. 381/86

* cited by examiner

*Primary Examiner* — Xu Mei
(74) *Attorney, Agent, or Firm* — Dickinson Wright PLLC

(57) ABSTRACT

A sound modification system and a method of managing sound in a vehicle. The system includes an active noise reduction (ANR) controller, an engine sound enhancement (ESE) controller and a sound modification controller. When the vehicle is in a steady state driving condition, the sound modification controller activates the ANR controller and deactivates the ESE controller. In contrast, when the vehicle is in a non-steady state driving condition, the sound modification controller activates the ESE controller and deactivates the ANR controller. Preferably, when the vehicle switches between the steady state and non-steady state driving conditions, the sound modification controller activates and deactivates the ANR and ESE controllers at a rate that is not noticeable to a human. In summary, the system utilizes the ANR and ESE controllers to achieve an optimal passenger cabin experience for the driver during any driving condition.

20 Claims, 2 Drawing Sheets

FIG. 1
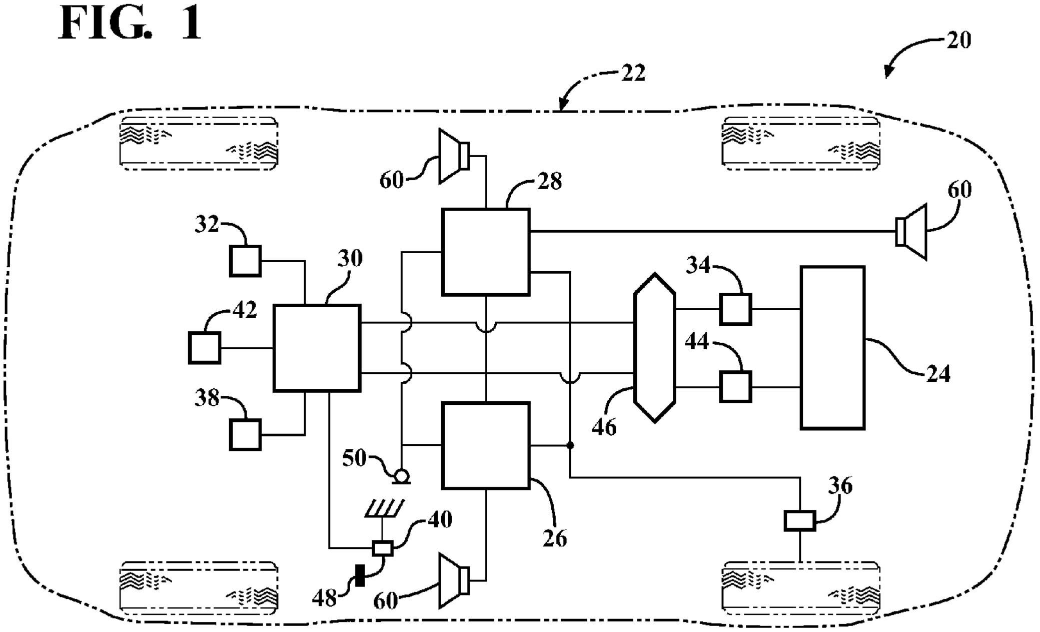
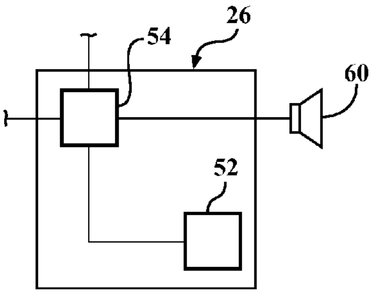
FIG. 2
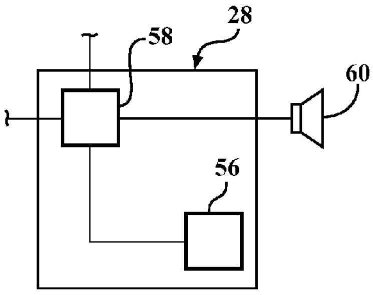
FIG. 3

SOUND MODIFICATION SYSTEM AND METHOD

BACKGROUND OF THE INVENTION

1. Field of the Invention

The invention relates to a sound modification system for modifying engine and road noises in vehicles. More specifically, the invention relates to a sound modification system for reducing noise; enhancing engine, exhaust and other desirable performance sounds; or a combination thereof.

2. Brief Description of the Prior Art

Automobile manufacturers continuously strive to reduce sound or noise levels in the passenger compartment of vehicles. Active noise reduction (ANR) systems have been developed to enable the audio system in the vehicle to introduce sound waves into the passenger compartment of a vehicle to cancel other sound waves, and thus, quiet the passenger compartment.

Some systems have been made that are capable of producing sounds that emulate performance sounds; however, these systems generally are not configured for a particular engine or are expensive to include in vehicles. In addition, as vehicle manufacturers have reduced noise, vibration and harshness (NVH) through various techniques, many enthusiasts miss hearing performance sounds which have also been reduced. More specifically, the more efficient engines and advanced technology now found in vehicles, many performance sounds are more difficult for a driver in the passenger compartment of the vehicle to hear. As such, there is a desire for a vehicle that has reduced NVH while still providing thrilling audio feedback to enthusiasts. Even further, electric cars have engines that are nearly silent to the human ear, and therefore, do not provide any audible engine noise. One negative of reduced engine noise is that many undesirable NVH sounds are now audible. Engine sound enhancement (ESE) systems have been developed to amplify such engine noises or other noises in electric vehicles for the safety of pedestrians. There is a significant and continuing need for improved ANR and ESE systems for vehicles to provide the driver of a vehicle with a more pleasurable acoustical atmosphere in the passenger compartment of the vehicle under a range of driving conditions.

SUMMARY OF THE INVENTION

The invention relates to a sound modification system for modifying engine and road noises in vehicles. More specifically, the invention relates to a sound modification system for reducing noise; enhancing engine, exhaust and other desirable performance sounds; or a combination thereof.

The invention provides for a sound modification system for a vehicle having a passenger compartment and a method for managing sound in a vehicle. The system includes a vehicle speed sensor for generating a vehicle speed signal, a vehicle acceleration sensor for generating a vehicle acceleration signal, a throttle position sensor for generating a throttle position signal and/or a cruise control sensor for generating a cruise control signal. The system also includes an active noise reduction (ANR) controller for generating an opposing sound wave signal substantially one hundred and eighty degrees (180°) out of phase with respect to a sound wave to be reduced, e.g. engine noise. The system further includes an engine sound enhancement (ESE) controller for selectively generating an engine enhancement sound wave signal substantially in phase with respect to a noise to be amplified, e.g. engine noise. The ANR and ESE controllers may be stand alone modules, one combined module or integrated into an amplifier or radio head unit. A loudspeaker is in communication with the ANR and ESE controllers for receiving the opposing sound wave signal and the engine enhancement sound signal and for outputting sound waves. The loudspeaker may be incorporated into the vehicle's entertainment system. The system also includes a sound modification controller in communication with the at least one sensor for receiving the vehicle speed signal, the vehicle acceleration signal, the throttle position signal and/or the cruise control signal and in communication with the ANR and ESE controllers. The sound modification controller automatically activates the ANR controller and deactivates the ESE controller in response to the vehicle being in a steady state driving condition, e.g. when the vehicle is travelling at a near-constant speed. The sound modification controller automatically activates the ESE controller and deactivates the ANR controller in response to the vehicle being in a non-steady state driving condition, e.g. accelerating. Alternatively, both the ANR and ESE controllers could be activated at the same time, depending on the driver's preference or selected driving mode, e.g. sport, luxury, performance, etc.

The method of controlling the sound in a vehicle having a passenger compartment includes the steps of sensing a driving condition of the vehicle as being either a steady state driving condition with the vehicle travelling at a near-constant speed or a non-steady state driving condition and outputting a first sound wave in response to the driving condition of the vehicle changing from the non-steady state driving condition to the steady state driving condition.

The invention is advantageous because, in the steady state driving condition, such as using cruise control or maintaining a constant speed on a highway, the occupants of the vehicle generally want the passenger compartment to minimize NVH and other noises. Therefore, the sound modification controller activates the ANR controller and deactivates the ESE controller, which results in a quieter passenger compartment. In contrast, at times, the driver wants to hear performance related sounds, such as the engine and other exhaust notes from the vehicle. During the non-steady state driving condition, the sound modification controller activates the ESE controller and deactivates the ANR controller. This amplifies desired performance sounds for the driver, and the sound modification controller controls the ANR and ESE controllers to achieve an optimal passenger compartment experience for the driver during any driving condition.

BRIEF DESCRIPTION OF THE DRAWINGS

The present invention will become more fully understood from the detailed description given here below, the appended claims, and the accompanying drawings in which:

FIG. 1 is a schematic drawing of the sound modification system in a vehicle;

FIG. 2 is a schematic drawing of an exemplary ANR controller;

FIG. 3 is a schematic drawing of an exemplary ESE controller; and

DETAILED DESCRIPTION OF THE ENABLING EMBODIMENTS

Figure 4:
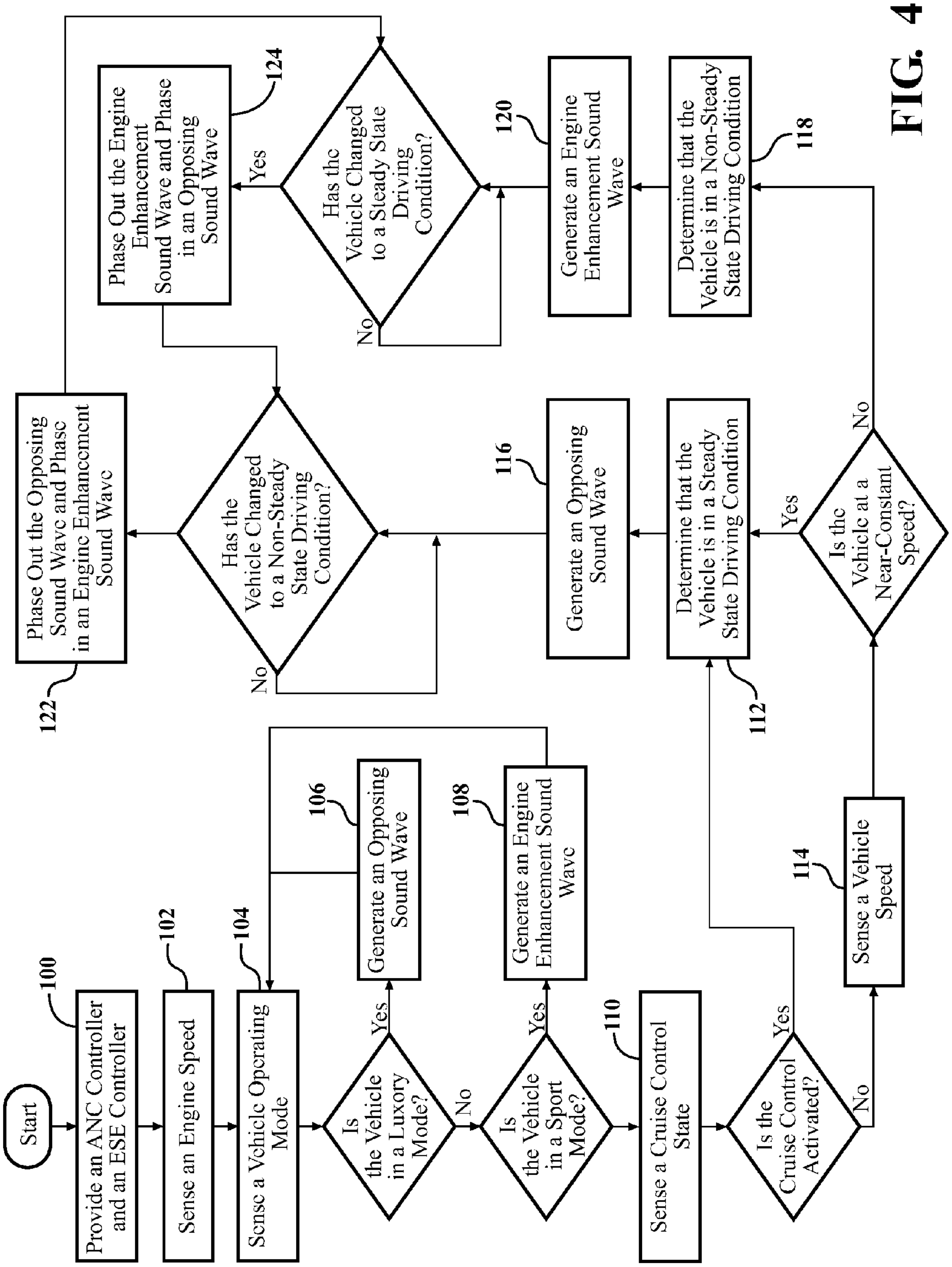
FIG. 4 is a flow chart of the exemplary method of managing the sound in a vehicle having a passenger compartment.

Referring to the Figures, wherein like numerals indicate corresponding parts throughout the several views, a sound modification system 20 for controlling audible noise in the passenger compartment of a vehicle 22 having an engine 24 is generally shown in FIG. 1. The system may be used in any type of vehicle 22, but is particularly applicable to automobiles, such as trucks, cars, sport utility vehicles, crossover vehicles and vans. The engine 24 of the vehicle 22 could be an internal combustion engine, an electric motor or any other type of engine.

The system of the exemplary embodiment includes an active noise reduction (ANR) controller 26 for reducing sound waves to quiet the passenger compartment of the vehicle 22; an engine sound enhancement (ESE) controller 28 for amplifying sounds; and a sound modification controller 30 for controlling the ANR and ESE controllers 26, 28. It should be appreciated that the ANR, ESE and sound modification controllers 26, 28, 30 could be separate units, or they could be contained within one unitary unit, e.g. a computer, amplifier module, radio head unit, etc.

The vehicle 22 of the exemplary embodiment includes a vehicle mode selector 32 for allowing the driver of the vehicle 22 to choose between a first mode, a second mode and a third mode. In the exemplary embodiment, the first mode is a sport mode, the second mode is a luxury mode and the third mode is an automatic mode. Of course, the types of selections may vary based on the type of vehicle or the desired operating modes. The vehicle mode selector 32 could be any type of input for allowing the driver to choose between the operating modes. For example, the vehicle mode selector 32 could be a switch or a knob in the passenger compartment of the vehicle 22. It should be appreciated that the vehicle mode selector 32 could have any number of different settings other than those of the exemplary embodiment and could be tied into the traction control system of the vehicle 22. For example, when a driver deactivates the traction control system of the vehicle 22, it could be akin to selecting the sport mode. The vehicle mode selector 32 generates a vehicle mode signal corresponding to the vehicle mode selected by the driver, the use of which will be described in further detail below.

The sound modification controller 30 is in communication with the vehicle mode selector 32 for receiving the vehicle mode signal. When the vehicle 22 is in the luxury mode, the sound modification controller 30 of the exemplary embodiment continuously operates the ANR controller 26 and deactivates the ESE controller 28. In other words, when the driver chooses the luxury mode, the ANR controller 26 reduces sound waves, and thus quiets, the passenger compartment of the vehicle 22.

When the vehicle 22 is in the sport mode, the sound modification controller 30 of the exemplary embodiment continuously operates the ESE controller 28 and deactivates the ANR controller 26. In other words, when the driver chooses the sport mode, the ESE controller 28 operates to continuously amplify engine sounds, or other sounds, in the passenger compartment.

The sound modification controller 30 of the exemplary embodiment is also configured to switch between operating the ANR and ESE controllers 26, 28 when the vehicle 22 is in the automatic mode. In the exemplary embodiment, the sound modification controller 30 alternates between the ANR and ESE controllers 26, 28 depending on the driving condition of the vehicle 22. Specifically, when the vehicle 22 is in a steady state driving condition, the sound modification controller 30 only activates the ANR controller 26 to quiet the passenger compartment of the vehicle 22. In contrast, when the vehicle 22 is in a non-steady state driving condition, then the sound modification controller 30 only activates the ESE controller 28 to amplify sounds in the passenger compartment of the vehicle 22. The steady state driving condition in this specification refers to a situation, such as cruise control, when the vehicle 22 is in a "steady state" of motion. For example, the steady state driving condition may be defined as when the vehicle speed remains at 55 mph, or when the vehicle 22 is travelling within a predetermined range of speed, e.g. ±5 mph. Alternatively, the steady state driving condition may be defined as when the magnitude of the vehicle acceleration remains less than one meter per second squared (1 $m/s^2$).

The sound modification controller 30 is configured to switch between the ANR and ESE controllers 26, 28 at a rate that is slow enough to not be noticeable to a human. In other words, the switching between the ANR and ESE controllers 26, 28 happens smoothly, and the driver or any other passengers in the passenger compartment of the vehicle 22 should not be able to tell when the sound modification controller 30 switches between the ANR and ESE controllers 26, 28. In the exemplary embodiment, the sound modification controller 30 fades in and out the ANR and ESE controllers 26, 28 at a rate of less than 3 decibels per second.

To determine whether the vehicle 22 is in the steady state driving condition, the sound modification controller 30 is in communication with a plurality of sensors 34, 36, 38, 40, 42, including for example, an engine speed sensor 34, a vehicle speed sensor 36, a vehicle acceleration sensor 38, a throttle position sensor 40 and a cruise control sensor 42. The vehicle speed sensor 36 senses the speed of the vehicle 22 and generates a vehicle speed signal. The vehicle acceleration sensor 38 senses the acceleration of the vehicle 22 and generates a vehicle acceleration signal. The throttle position sensor 40 senses the position of a throttle pedal 48 in the vehicle 22 and generates a throttle position signal. The cruise control sensor 42 senses whether the cruise control system in the vehicle 22 is operating or deactivated and generates a cruise control signal. The sound modification controller 30 of the exemplary embodiment can use these sensors 34, 36, 38, 40, 42 and their respective outputs to calculate the driving condition of the vehicle 22 according to a predetermined algorithm, as will be discussed in further detail below. The sound modification controller 30 of the exemplary embodiment is also in communication with an engine control unit 44 (ECU) through a controller area network 46 (CAN) bus to provide an additional input to the algorithm. It should be appreciated that the sound modification controller 30 could be in communication with a number of different sensors in addition to or in place of those shown in the exemplary embodiment for determining if the vehicle 22 is in the steady state driving condition.

The engine speed sensor 34 is operatively coupled to the engine 24 of the vehicle 22 and generates an engine speed signal. Typically, the engine speed sensor 34 measures the speed of the engine in revolutions per minute (RPM). A variety of other sensors could also be coupled to the engine 24 for monitoring other conditions. For example, the various sensors could measure the torque being produced by the engine 24, the power being produced by the engine 24, the temperature of the engine 24, etc. These sensors could also be in communication with the sound modification controller 30 and used in the algorithm to determine the driving condition of the vehicle 22.

The sound modification controller 30 uses an algorithm that automatically determines that the vehicle 22 is in a steady state driving condition whenever the cruise control system is activated. Thus, when the vehicle 22 is in the automatic mode and the cruise control system is activated to keep the vehicle 22 at a near-constant speed, the ANR controller 26 remains activated and the ESE controller 28 remains deactivated.

The algorithm of the sound modification controller 30 can also determine if the vehicle 22 is in a steady state driving condition when the cruise control system is not activated. In the exemplary embodiment, the sound modification controller 30 determines that the vehicle 22 is in a steady state driving condition when the vehicle 22 remains within a five mile per hour range (±5 mph) for greater than five minutes. Alternatively, the algorithm could use the outputs of other sensors 34, 36, 38, 40, 42 to determine the driving condition of the vehicle. For example, if the throttle pedal 48 remains at a position for a predetermined period of time, the sound modification controller 30 would determine that the vehicle 22 is in the steady state driving condition. Similarly, if the engine 34 remains within a predetermined non-idle speed range for a predetermined time, then the sound modification controller 30 would determine that the vehicle 22 is in the steady state driving condition.

The ANR controller 26 of the exemplary embodiment is in communication with the engine speed sensor 34 of the engine for receiving the engine speed signal and to at least one microphone 50 disposed either in the passenger compartment, the engine compartment or exterior of the vehicle 22. As shown in FIG. 2, the ANR controller 26 of the exemplary embodiment includes an ANR memory 52 for storing a noise profile of the engine and an ANR processor 54 for generating an opposing sound wave signal. The ANR processor 54 generates the opposing sound wave signal as a function of the engine speed signal and the sound received by the microphone 50. The opposing sound wave signal is substantially one hundred and eighty degrees (180°) out of phase with the sound waves being reduced. The noise profile of the engine is preferably a pre-set profile of the sounds produced by the engine 24 at various engine speeds. Thus, with the engine profile, the ANR controller 26 can generate an opposing sound wave signal to reduce the noise produced by the engine 24 solely as a function of engine speed. Preferably, when the sound modification controller 30 phases in the ANR controller 26, the ANR controller 26 progressively increases the amplitude of the opposing sound wave signal until the opposing sound wave signal has an amplitude substantially equal to the amplitude of the sound waves produced by the engine 24 at a rate that is not noticeable to a human, e.g. less than 3 decibels per second. Alternatively, the ANR controller 26 could be configured to only reduce, and not entirely cancel sound waves by increasing the amplitude of the opposing sound to a level that is less than the amplitude of the sound wave being quieted. This is useful, for example, to allow the occupants of the passenger compartment to hear a subtle rumble of the engine 24. Likewise, when the ANR controller 26 is phased out, or deactivated, the ANR controller 26 progressively decreases the amplitude of the opposing sound wave signal.

In addition to the engine speed sensor 34 and the microphone 50, the ANR controller 26 may also use other inputs to generate the opposing sound wave signal. For example, the ANR controller 26 could use the engine ECU 44, the vehicle speed sensor 36, the vehicle acceleration sensor 38 or the throttle position sensor 40 as additional inputs for generating the opposing sound wave signal. With these inputs, the opposing sound wave signal could reduce more noises than just the engine noise. For example, the ANR controller 26 could be configured to also reduce transmission noises, differential noises, road noises, wind noises or any other noises coming from outside of the passenger compartment of the vehicle 22.

The ANR controller 26 could be configured to reduce noises over a predetermined frequency range, a plurality of frequency ranges or for the complete audible noise spectrum. The ANR controller 26 could also be configured to only reduce noises above a predetermined noise level. The determination of what noise level to review may depend on a variety of vehicle status signals. For example, when the vehicle 22 is traveling above a set speed and the windows are open, the ANR controller 26 may only look for a narrow range of noise levels as all other noise levels the ANR controller 26 would typically look for may be irrelevant due to the noise from the windows. These parameters of when to look for particular noise levels and when not to look for particular noise levels may be set by the vehicle manufacturer.

The ESE controller 28 is in communication with the engine speed sensor 34 of the engine for receiving the engine speed signal and to a microphone 50 disposed either in the passenger compartment, the engine compartment or exterior of the vehicle 22. As shown in FIG. 3, the ESE controller 28 of the exemplary embodiment includes an ESE memory 56 for storing a noise profile of the engine and an ESE processor 58 for generating an engine enhancement sound wave signal. The engine enhancement sound wave signal is substantially in phase with the noise being produced by the engine 24, or any other noise to be amplified. The noise profile of the engine 24 is a pre-set profile of the sounds produced by the engine at various engine speeds. Thus, with the engine profile, the ESE controller 28 can generate an engine enhancement sound wave signal for amplifying engine noise solely as a function of engine speed. The engine enhancement sound wave signal can have any amplitude depending on the desired level of amplification. Preferably, when the sound modification controller 30 phases in the ESE controller 28, the ESE controller 28 progressively increases the amplitude of the engine enhancement wave signal until the opposing sound wave signal to the desired level of amplification at a rate that is not noticeable to a human, e.g. less than 3 decibels per second. Likewise, when the ESE controller 28 is phased out, or deactivated, the ESE controller 28 progressively decreases the amplitude of the opposing sound wave signal at a rate that is not noticeable to a human.

In addition to the engine speed sensor 34 and the microphone 50, the ESE controller 28 may also use other inputs to generate the engine enhancement sound wave signal. For example, the ESE controller 28 could use the engine ECU 44, the vehicle speed sensor 36, the vehicle acceleration sensor 38 or the throttle position sensor 40 as additional inputs for generating the engine enhancement sound wave signal. With these inputs, the engine ESE controller 28 could amplify more noises than just the engine noise. For example, the ESE controller 28 could be configured to amplify tire squeal noises, the whine of a turbo/supercharger or any other noises.

The ANR and ESE controllers 26, 28 are in communication with at least one loudspeaker 60 in the passenger compartment. The loudspeaker 60 in the passenger compartment receives the opposing sound wave signal and the engine enhancement sound wave signal and outputs sound waves into the passenger compartment. The loudspeaker 60 could be disposed anywhere within the passenger compartment of the vehicle 22, including on the headrests of the seats in the vehicle 22. The ESE controller 28 may also be in communication with at least one loudspeaker 60 on the exterior of the vehicle 22 for projecting sound waves outside of the vehicle 22. It should be appreciated that the loudspeaker 60 in the interior of the vehicle 22 could be a part of the vehicle's entertainment system and does not have to be separately dedicated to noise cancellation and/or enhancement.

The invention further provides a method of controlling the sound in the passenger compartment of a vehicle 22. The method of the exemplary embodiment starts with the step 100 of providing an ANR controller 26 and an ESE controller 28. The method continues with the step 102 of sensing an engine speed of the engine 24. As explained above, in the exemplary embodiment, the engine speed of the vehicle 22 is determined with an engine speed sensor 34.

The method then continues with the step 104 of sensing a vehicle 22 operating mode. In the exemplary embodiment, the operating modes are a sport mode, a luxury mode and an automatic mode. If the vehicle 22 is in the luxury mode, then the method proceeds with the step 106 of generating with the ANR controller 26 a continuous opposing sound wave having an amplitude substantially equal to the amplitude of a sound wave to be reduced and substantially one hundred and eighty degrees (180°) out of phase with the sound waves to be reduced. As described above, alternately, the ANR controller 26 could quiet, rather than cancel, noise. If the ANR controller 26 is reducing noise, then the opposing sound wave will have an amplitude smaller than the amplitude of the sound wave to be quieted. If the sound wave to be reduced is noise from the engine of the vehicle 22, then the ANR controller 26 could generate the opposing sound wave as a function of the sensed engine speed. It should be appreciated that the sound wave to be reduced could be from other sources than the engine 24, e.g. road noise or wind noise.

If the vehicle 22 is in the sport mode, then the method proceeds with the step 108 of sensing a sound wave to be amplified and generating with the ESE controller 28 a continuous engine enhancement sound wave substantially in phase with a sound wave to be amplified. If the sound wave to be amplified is noise coming from the engine 24 of the vehicle 22, then the ESE controller 28 could generate the engine enhancement sound wave as a function of the sensed engine speed. However, it should be appreciated that the sound wave to be amplified could come from sources other than the engine 24, e.g. the tires.

If the vehicle 22 is in the automatic mode, then the method continues with the step 110 of sensing a cruise control state of the vehicle 22 as one of activated or deactivated. In other words, the method determines whether the driver is using a cruise control system in the vehicle 22 to maintain a near-constant speed. If the cruise control system of the vehicle 22 is activated, then the method continues with the step 112 of determining that the vehicle 22 is in a steady state driving condition.

If the vehicle 22 is in the automatic mode and the cruise control system is deactivated, then the method continues with the step 114 of sensing a vehicle speed of the vehicle 22. The method then continues with the step 112 of determining that the vehicle 22 is in a steady state driving condition in response to the vehicle 22 speed remaining within a predetermined range for a predetermined period of time. In other words, the vehicle 22 is in a steady state driving condition if it remains at a near-constant speed. For example, the steady state driving condition could be when the vehicle 22 stays within a five mile per hour range (±5 mph) for greater than five minutes.

If the vehicle 22 is in the automatic mode and the steady state driving condition, then the method continues with the step 116 of sensing a sound wave to be reduced and generating with the ANR controller 26 an opposing sound wave having an amplitude substantially equal or less than the sound wave to be reduced and substantially one hundred and eighty degrees (180°) out of phase with respect to the sound wave to be reduced.

If the vehicle 22 is in the automatic mode and is not in the steady state driving condition, then the method continues with the step 118 of determining that the vehicle is in a non-steady state driving condition. The method then continues with the step 120 of sending a sound wave to be amplified and generating with the ESE controller 28 an engine enhancement sound wave substantially in phase with a sound wave to be amplified.

Steps 110 and 114 are performed continuously or periodically while the vehicle 22 is in the automatic mode. Therefore, any change in the driving condition of the vehicle 22 will be detected. If the vehicle 22 leaves the steady state driving condition, then the method continues with the step 122 of progressively decreasing the amplitude of the opposing sound wave and generating with the engine sound controller and progressively increasing the amplitude of an engine enhancement sound wave substantially in phase with a sound wave to be amplified. In other words, the engine enhancement sound wave is phased in simultaneously to the opposing sound wave being phased out when the vehicle 22 transitions from the steady state driving condition to the non-steady state driving condition. Also in the exemplary embodiment, the phasing out of the opposing sound wave and the phasing in of the engine enhancement sound wave take place at a rate that is not noticeable to a human. Specifically, in the exemplary embodiment, the opposing and engine enhancement sound waves are phased in/out at a rate of less than 3 decibels per second.

If the vehicle 22 transitions from the non-steady state driving condition to the steady state driving condition, then the method continues with the step 124 of progressively decreasing the amplitude of the engine enhancement sound wave and generating with the ANR controller 26 and progressively increasing the amplitude of the opposing sound wave. In the exemplary embodiment, the phasing out of the engine enhancement sound wave and the phasing in of the opposing sound wave take place at a rate that is not noticeable to a human, e.g. less than 3 decibels per second.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

What is claimed is:

1. A method of controlling the sound in a vehicle having a passenger compartment comprising the steps of:

sensing a driving condition of the vehicle as being one of a steady state driving condition with the vehicle travelling at a near-constant speed and a non-steady state driving condition, and based on the sensing of the driving condition, either:

outputting into the passenger compartment a noise cancelling sound wave to cancel at least one sound in the passenger compartment of the vehicle in response to sensing the steady state driving condition with the vehicle travelling at a near-constant speed, or outputting into the passenger compartment a noise amplifying sound wave to amplify at least one sound in the passenger compartment in response to the vehicle changing from the steady state driving condition with the vehicle traveling at a near-constant speed to the non-steady state driving condition, wherein the noise amplifying sound wave is a performance sound for a driver of the vehicle.

2. The method of controlling the sound in a vehicle as set forth in claim 1 wherein the step of outputting a noise cancelling sound wave is further defined as generating and progressively increasing the amplitude of a first sound wave from zero amplitude to a predetermined amplitude in response to the driving condition of the vehicle changing from the non-steady state driving condition to the steady state driving condition.

3. The method of controlling the sound in a vehicle as set forth in claim 2 wherein the step of progressively increasing the amplitude of the noise cancelling sound wave takes place at a rate of less than 3 decibels per second.

4. The method of controlling the sound in a vehicle as set forth in claim 3 wherein the step of progressively increasing the amplitude of the noise cancelling sound wave takes place over a period greater than sixty seconds.

5. The method of controlling the sound in a vehicle as set forth in claim 1 further including the step of sensing a sound wave to be reduced and wherein the noise cancelling sound wave is an opposing sound wave substantially one hundred and eighty degrees out of phase with respect to the sound wave to be reduced.

6. The method of controlling the sound in a vehicle as set forth in claim 5 further including the step of sensing an engine speed of an engine of the vehicle and wherein the step of outputting the noise cancelling sound wave is further defined as outputting an opposing sound wave substantially one hundred and eighty degrees out of phase with respect to the sound waves of the engine at the sensed engine speed according to an engine profile.

7. The method of controlling the sound in a vehicle as set forth in claim 1, wherein the step of outputting a noise amplifying sound wave is further defined as outputting and progressively increasing the amplitude of a noise amplifying sound wave in response to the driving condition of the vehicle changing from the steady state driving condition to the non-steady state driving condition.

8. The method of controlling the sound in a vehicle as set forth in claim 7 wherein the noise amplifying sound wave is an engine enhancement sound wave substantially in phase with a noise to be amplified.

9. The method of controlling the sound in a vehicle as set forth in claim 8 further including the step of sensing an engine speed of an engine of the vehicle and wherein the step of outputting the engine enhancement sound wave is further defined as outputting an engine enhancement sound wave substantially in phase with the selected sound waves of the engine at the sensed engine speed according to an engine profile.

10. The method of controlling the sound in a vehicle as set forth in claim 1 further including the steps of sensing a cruise control state of the vehicle and determining that the vehicle is in the steady state driving condition in response to the cruise control of the vehicle being activated.

11. The method of controlling the sound in a vehicle as set forth in claim 1 further including the steps of sensing a vehicle speed and determining that the vehicle is in the steady state driving condition in response to the vehicle speed remaining within a predetermined range for a predetermined period of time.

12. The method of controlling the sound in a vehicle as set forth in claim 11 wherein the predetermined range is ±5 miles per hour and wherein the predetermined period of time is five minutes.

13. The method of controlling the sound in a vehicle as set forth in claim 1, wherein the engine enhancement sound is at least one of: an engine noise, a tire squeal noise, and a whine of a turbo/supercharger.

14. A sound modification system for a vehicle having a passenger compartment comprising:

at least one sensor for sensing a condition of the vehicle and for generating a condition signal;

at least one controller in communication with said sensor for receiving said condition signal and configured to determine a driving condition of the vehicle as one of a steady state driving condition with the vehicle travelling at a near-constant speed and a non-steady state driving condition and configured to generate a noise cancelling sound wave signal in response to said driving condition of the vehicle being said steady state driving condition and configured to generate a noise amplifying sound wave signal in response to said driving condition of the vehicle being said non-steady state driving condition; and based on the sensed condition, outputting via at least one loudspeaker in communication with said controller for receiving said noise cancelling and noise amplifying sound wave signals, either sound waves corresponding to said noise cancelling to cancel a noise in the passenger compartment while the vehicle is in said steady state driving condition, or noise amplifying sound wave signals to amplify a noise in the passenger compartment while the vehicle is in said non-steady state driving wherein the noise amplifying sound wave signals is a performance sound for a driver of the vehicle.

15. The sound modification system as set forth in claim 14 wherein said sensor is one of an engine speed sensor and a vehicle speed sensor and a vehicle acceleration sensor and a throttle position sensor and a cruise control sensor.

16. The sound modification system as set forth in claim 14 wherein said at least one controller is an active noise reduction controller and said noise cancelling sound wave signal is an opposing sound wave signal substantially one hundred and eighty degrees out of phase with respect to a sound wave to be cancelled.

17. The sound modification system as set forth in claim 16 further including an engine speed sensor for sensing an engine speed and for generating an engine speed signal.

18. The sound modification system as set forth in claim 17 wherein said engine speed sensor is in communication with said active noise reduction controller and wherein said active noise reduction controller is configured to generate said noise cancelling sound wave signal substantially one hundred and eighty degrees out of phase with respect to the sound waves produced by the engine at the sensed engine speed according to an engine profile.

19. The sound modification system as set forth in claim 17 further including an engine sound enhancement controller in communication with said loudspeaker and wherein said noise amplifying sound wave signal is an engine enhancement sound wave signal substantially in phase with a sound wave to be amplified in response to said driving condition of the vehicle being said non-steady state driving condition.

20. The sound modification system as set forth in claim 19 wherein said engine sound enhancement controller is in communication with said engine speed sensor and wherein said engine sound enhancement controller is configured to generate said engine enhancement sound wave signal substantially in phase with respect to the sound waves produced by the engine at the sensed speed according to an engine profile.

* * * * *